(12) United States Patent
Sharma et al.

(10) Patent No.: US 6,491,709 B2
(45) Date of Patent: Dec. 10, 2002

(54) ALTERNATE-SITE LANCER

(75) Inventors: Ashutosh Sharma, Springfield, NJ (US); Amir A. Sharifi-Mehr, Bloomingdale, NJ (US); Robert E. West, Basking Ridge, NJ (US); Robert J. Strowe, Ramsey, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 39 days.

(21) Appl. No.: 09/745,947

(22) Filed: Dec. 22, 2000

(65) Prior Publication Data

US 2002/0082521 A1 Jun. 27, 2002

(51) Int. Cl.7 .................................................. A61B 17/34
(52) U.S. Cl. ................................... 606/181; 604/164.06
(58) Field of Search .......................... 600/576; 606/181, 606/183; 604/164.06

(56) References Cited

U.S. PATENT DOCUMENTS

| | | | | |
|---|---|---|---|---|
| 4,565,545 A | * | 1/1986 | Suzuki | 604/164.06 |
| 4,967,763 A | * | 11/1990 | Nugent et al. | 600/576 |
| 5,116,353 A | * | 5/1992 | Green | 604/164.06 |
| 5,353,806 A | * | 10/1994 | Heinzelman et al. | 600/576 |
| 5,454,828 A | * | 10/1995 | Schraga | 606/181 |
| 5,552,117 A | * | 9/1996 | Burns | 600/576 |
| 5,879,311 A | * | 3/1999 | Duchon et al. | 606/181 |
| 5,951,493 A | | 9/1999 | Douglas et al. | 600/583 |
| 6,071,250 A | * | 6/2000 | Douglas et al. | 606/181 |
| 6,106,539 A | * | 8/2000 | Fortier | 604/164.06 |

* cited by examiner

Primary Examiner—Paul J. Hirsch
(74) Attorney, Agent, or Firm—Alan W. Fielder

(57) ABSTRACT

A new tip for a conventional lancer that provides for improved blood flow from a lancet puncture site not located on a patient's finger. The new lancer tip includes a plurality of crenellations that exert rotational force on the skin surrounding the lancet puncture site when the lancer is rotated to enhance blood flow from the lancet puncture site.

13 Claims, 7 Drawing Sheets

ALTERNATE-SITE LANCER

BACKGROUND OF THE INVENTION

The present invention relates to a lancer for withdrawing a sample of blood from a patient via a lancet. More particularly, the invention is drawn to a lancer for obtaining blood samples from alternate sites, i.e., an arm, leg, or sites other than the fingertip, for the purpose of measuring the concentration of an analyte in blood, i.e., glucose.

Conventional lancers on the market are designed to sample blood to determine an analyte in blood such as glucose. These conventional lancers use a finger blood-sampling approach which can be quite painful for the patient because of the concentration of nerves that are present on fingertips. Some companies are developing lancer technology to obtain blood samples from sites other than fingertips ("alternate sites"). Such alternate sites include arms and legs which have a smaller concentration of nerves thus resulting in less pain being associated with the blood sampling process. However, the problem with these alternate sites in that they do not bleed as easily or as well as sites on the finger when pierced using fine gauge lancets. Therefore, there is the need for a new lancer mechanism that can obtain sufficient blood samples from these alternate sites.

SUMMARY OF THE INVENTION

The present invention is drawn to an improved lancer having features that increase the capability of drawing blood from alternate sites. The present invention forces or milks blood from the lancet puncture on an alternate site by using a twisting motion to act as the mechanism to force blood from the alternate site. During operation, the user activates the lancer to create a lancet puncture in the alternate site, i.e., arm or leg. Once a puncture is created, the user twists the device approximately ¼ of a rotation while the alternate site tip is against the patient's skin. The user maintains the twisting force for several seconds while fingers, crenellations (castle-like features) or trapezoid features on the alternate site cap grab the skin and apply a twisting motion to the patient's skin. The twisting motion on the skin causes the puncture wound to bleed at a higher volume than if no twisting is applied. The twisting action is analogous to wringing a wet towel to force water from the fibers of the towel.

In addition, the alternate site cap also provides an advantage in that it is removable which allows the user to use the lancer as a conventional lancer when the conventional cap is attached.

Another feature of the present invention to enhance blood flow is provided by the new chisel point geometry of the lancet.

These and other aspects, features and advantages of the present invention, will become apparent from the following detailed description taken in conjunction with the accompanying drawings.

DETAILED DESCRIPTION

Lancer devices are typically used to obtain a blood sample from a patient by piercing the skin so that a small amount of blood can be withdrawn. For example, ballistic-type lancer devices are typically designed to be used in conjunction with narrow gauged lancets to obtain a drop of capillary blood from a finger for use in a low-volume blood glucose monitor. The present invention is directed to obtaining a blood sample from an alternate site, i.e., arm or leg, and will draw approximately 0.5 micro-liter of blood.

Figure 1:
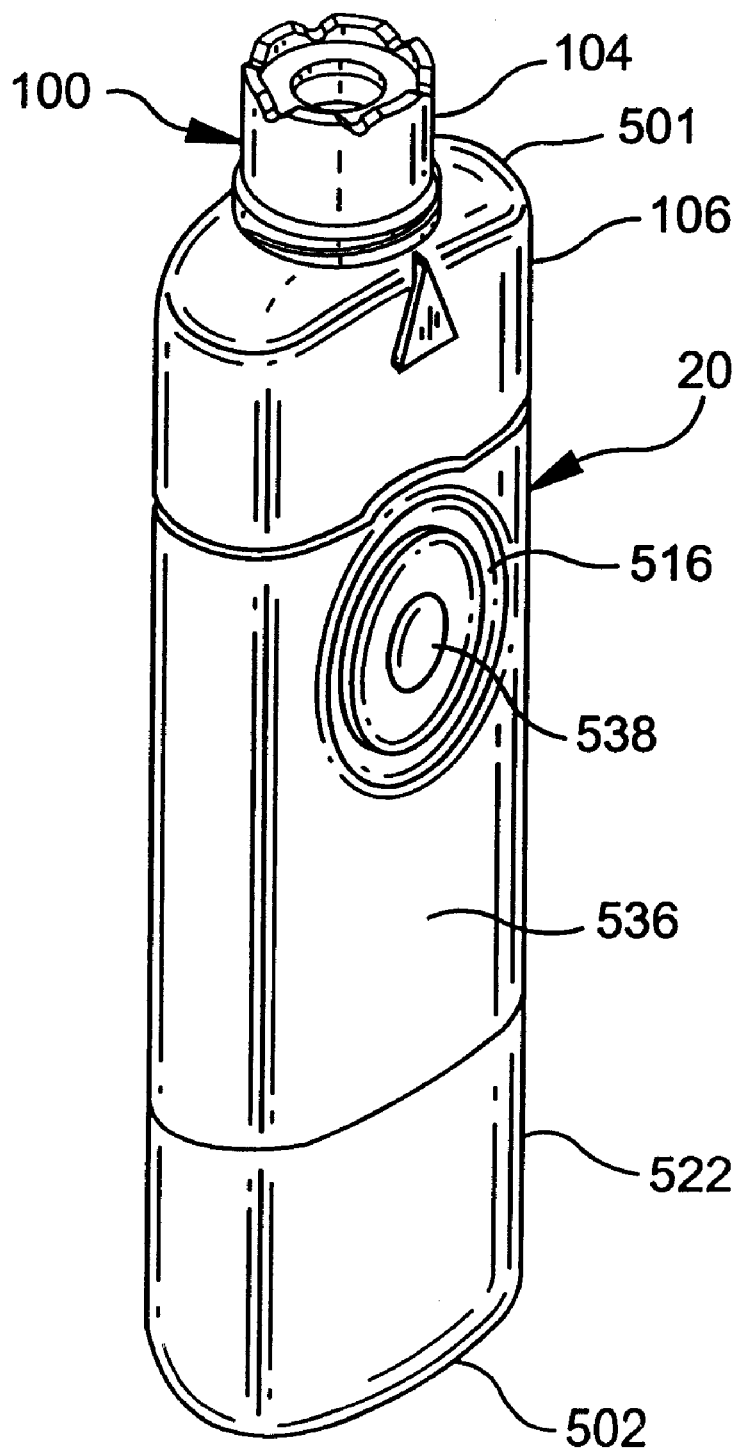
FIG. 1 shows a perspective view of a lancer device having an alternate site cap tip.

FIG. 1 shows a perspective view of a lancer device 20. Device 20 has an oblong shaped body 536 having a distal end 501 and a proximal end 502. Body 536 includes an orifice 516 which provides access to a trigger or button 538 that is used to fire a lancet 300 within device 20. An end knob 522 extends from proximal end 502 of body 536 and is used to arm device 20 prior to firing the lancet with trigger 538. An alternate site cap tip 100 is attached to distal end 501 of body 536.

Figure 2:
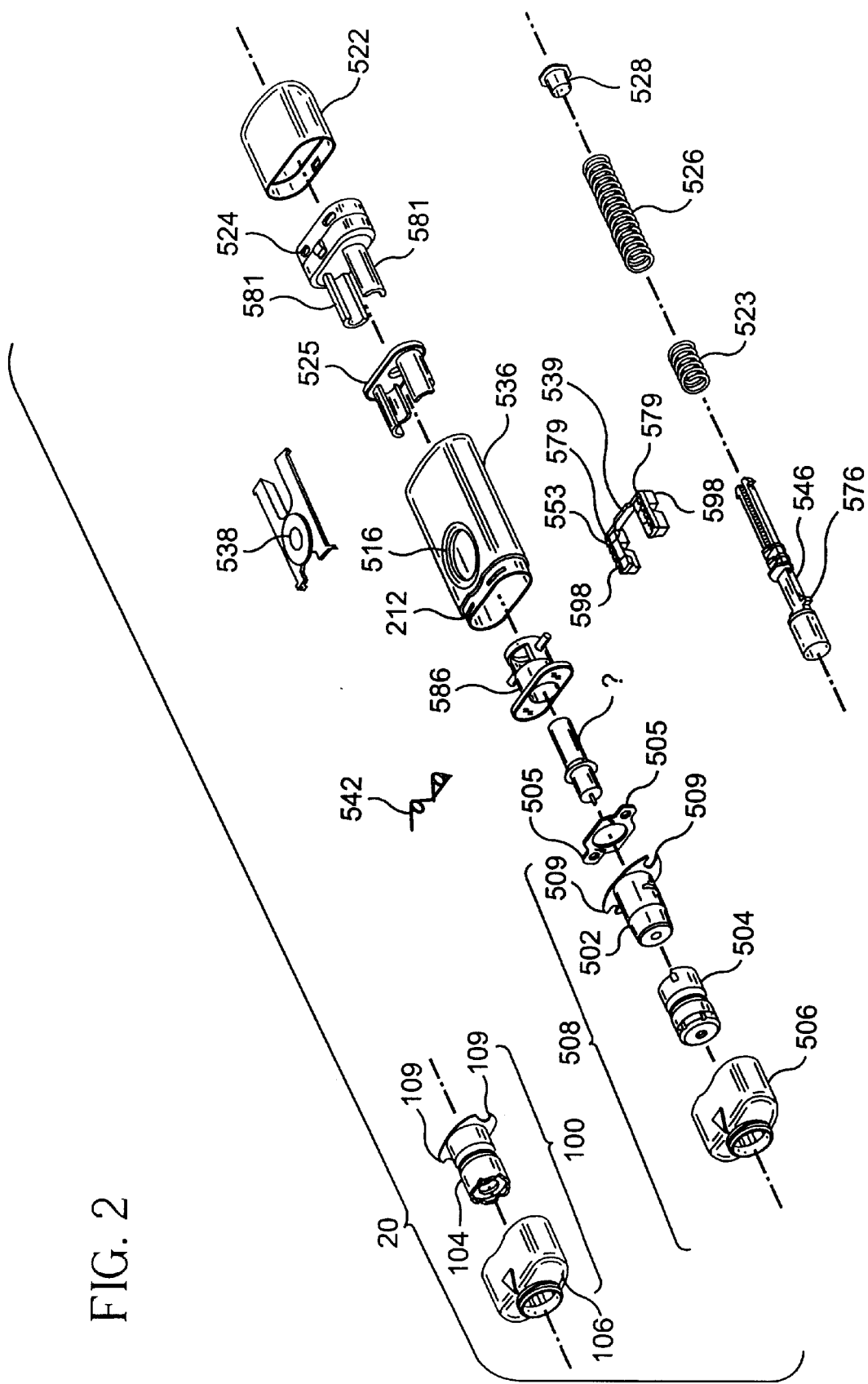
FIG. 2 shows an exploded perspective view of the lancer device, the alternate site cap tip, and a conventional adjustable cap tip.

FIG. 2 shows an exploded view of lancer device 20. Lancer 20 has an oblong outer body section 536 connected to an end knob 522. End knob 522 is used for arming or cocking the device 20 and is sized to be compatible with the oblong shaped body 536. Body section 536 suitably has an orifice 516 in which a release means, such as a trigger or button 538, is mounted. Disposed within body 536 is a plunger or shaft 546. An alternate site cap tip 100 includes a nose portion 106 with an alternate site tip 104.

In addition, the alternate site cap tip 100 also provides an advantage in that it is removable which allows the user to use lancer 20 as a conventional lancer when a conventional cap tip 508 is attached. FIG. 2 shows a conventional tip assembly 508 having an inner member 502, outer adjustment member 504, and nose portion 506. Conventional tip assembly 508 can be detached from the body assembly 536. Adjustment member 504 is constrained from linear motion in nose portion 506 and only moves radially. The inner member, also referred to as a lancet stop 502, has a full thread-form mating into the adjustment member 504. The user rotates adjustment member 504 radially to change the relative distance between the adjustment member 504 and the lancet stop 502. The slots 509 interact with posts 201 shown in FIG. 4 to prevent radial motion of stop 502 and permit stop 502 to move only axially due to the camming motion of the thread forms.

When armed, yoke latch 539 retains one or more tangs (shown as a single tang 576) of plunger 546 in yoke latch window 553. Yoke latch 539 is mounted to sleeve 586. Mounting points 598 on yoke latch 539, which are for example, apertures in yoke latch 539, attach to posts 504 of sleeve 586. These mounting points 598 form a pivot axis when yoke latch 539 is actuated. Actuation is achieved by overcoming biasing means 542 to release yoke latch 539. Yoke latch 539 is pivoted about the pivot axis against biasing means 542, which is suitably a spring. This causes yoke latch 539 to move perpendicular to the axis of the device 20, enabling tang 576 on plunger 546 to pass through window 553 of yoke latch 539. After actuation, proximal fingers 579 on the yoke latch 539 abut distal fingers 581 of the inner knob 524, thereby preventing engagement of the yoke latch 539 on tang 576 of the plunger 546. The device can be armed by retracting end knob 522 in the proximal direction since this will cause the distal fingers 581 of inner knob 524 to disengage the yoke latch proximal fingers 579 so that yoke latch 539 can engage tang 576 on plunger 546. This is accomplished by yoke latch 539 pivoting about the pivot axis to a position in which yoke latch 539 can engage tang 576. Triggering spring 523 and return spring 526 perform triggering and return functions, respectively. Retainer 528 facilitates retraction of the plunger 546, members 505 provide support for the posts, and member 525 provides alignment for fingers 581.

Figure 3:
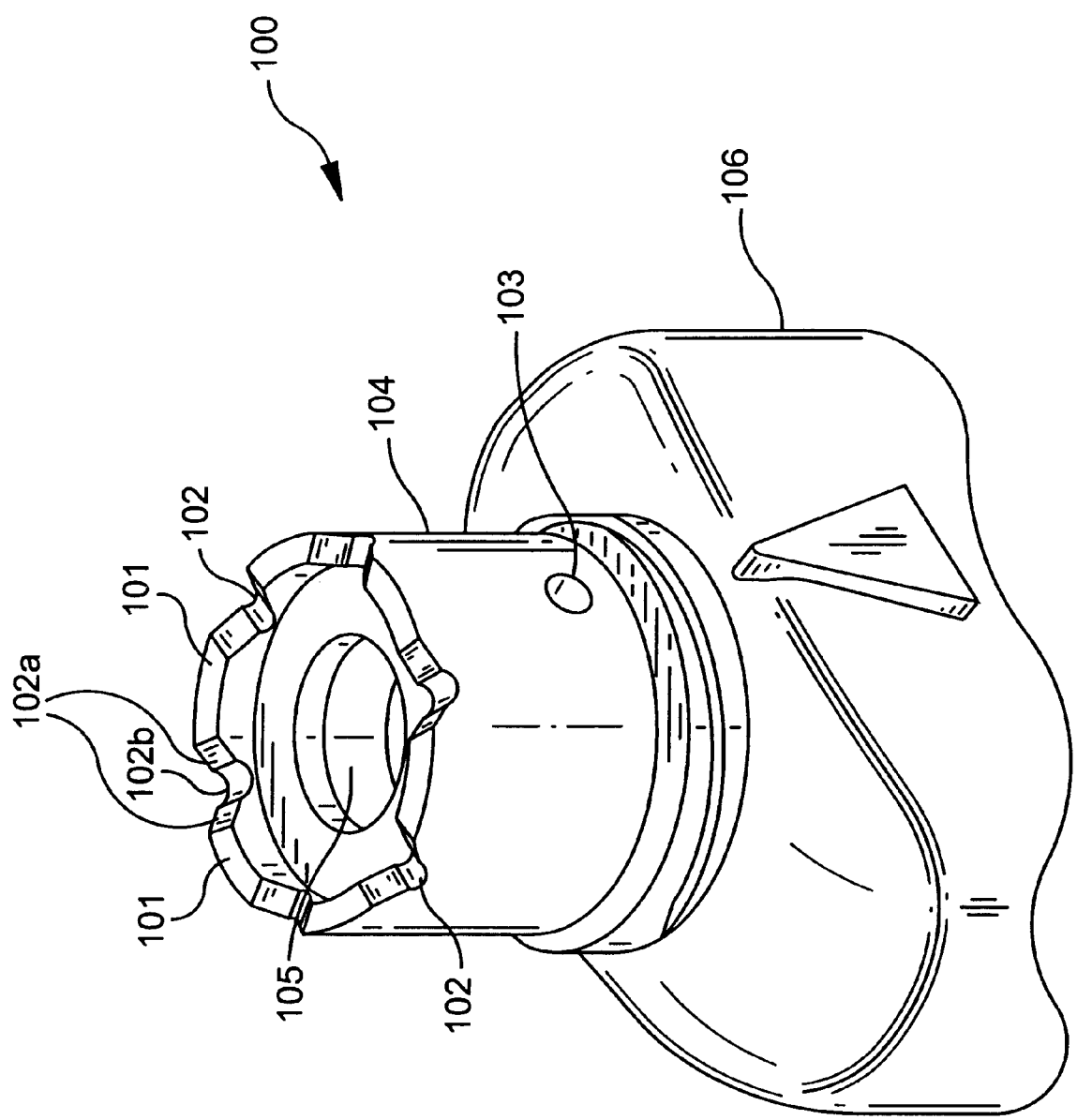
FIG. 3 shows an enlarged perspective view of the crenellations (castle-like/trapezoid features) on the alternate site cap tip.

FIG. 3 shows an enlarged perspective view of alternate site cap tip 100 with its nose portion 106 and alternate site tip 104. The present invention uses alternate site cap tip 100 to force or milk blood from the lancet puncture on an alternate site by using a twisting motion to act as the mechanism to force blood from the alternate site. Alternate site tip 104 includes a black dot or measuring indicia 103 or other visual indicators, such as parallel lines separated by the diameter of the blood drop, that the user uses to determine when the proper volume of blood has been extracted. Alternate site tip 104 is transparent so that the user can see the drop of blood that is being drawn and compare it to measuring indicia 103 on alternate site tip 104.

FIG. 3 also shows fingers or crenellations (castle-like/trapezoid features) 101 extending from the distal end of alternate site tip 104 separated by depressions 102 having angle ramp surfaces 102a and a curved middle portion 102b. The geometry of the distal end of the alternate site tip 104 grabs the user's skin and by applying approximately a ¼ turn by twisting body 536, alternate site tip 104 helps milk the lanced site and force blood to come out for testing. The inventors have found that twisting around the circumference of the lancet site produces a higher blood volume compared to conventional methods not using twisting. In addition, the inventors have found that using the twisting method with the alternate site tip 104 of the present invention provides even more blood volume over any other methods and devices currently known.

During operation, the user activates lancer 20 to create a lancet puncture in the alternate site, i.e., arm or leg. Once a puncture is created, the user twists body 536 approximately ¼ of a rotation while alternate site tip 104 is against the patient's skin. The user maintains the twisting force for several seconds while crenellations 101 on alternate site tip 104 grab the skin and apply a twisting motion to the patient's skin. The twisting motion on the skin causes the puncture wound to bleed at a higher rate than if no twisting is applied. The twisting action is analogous to wringing a wet towel to force water from the fibers of the towel.

Figure 4:
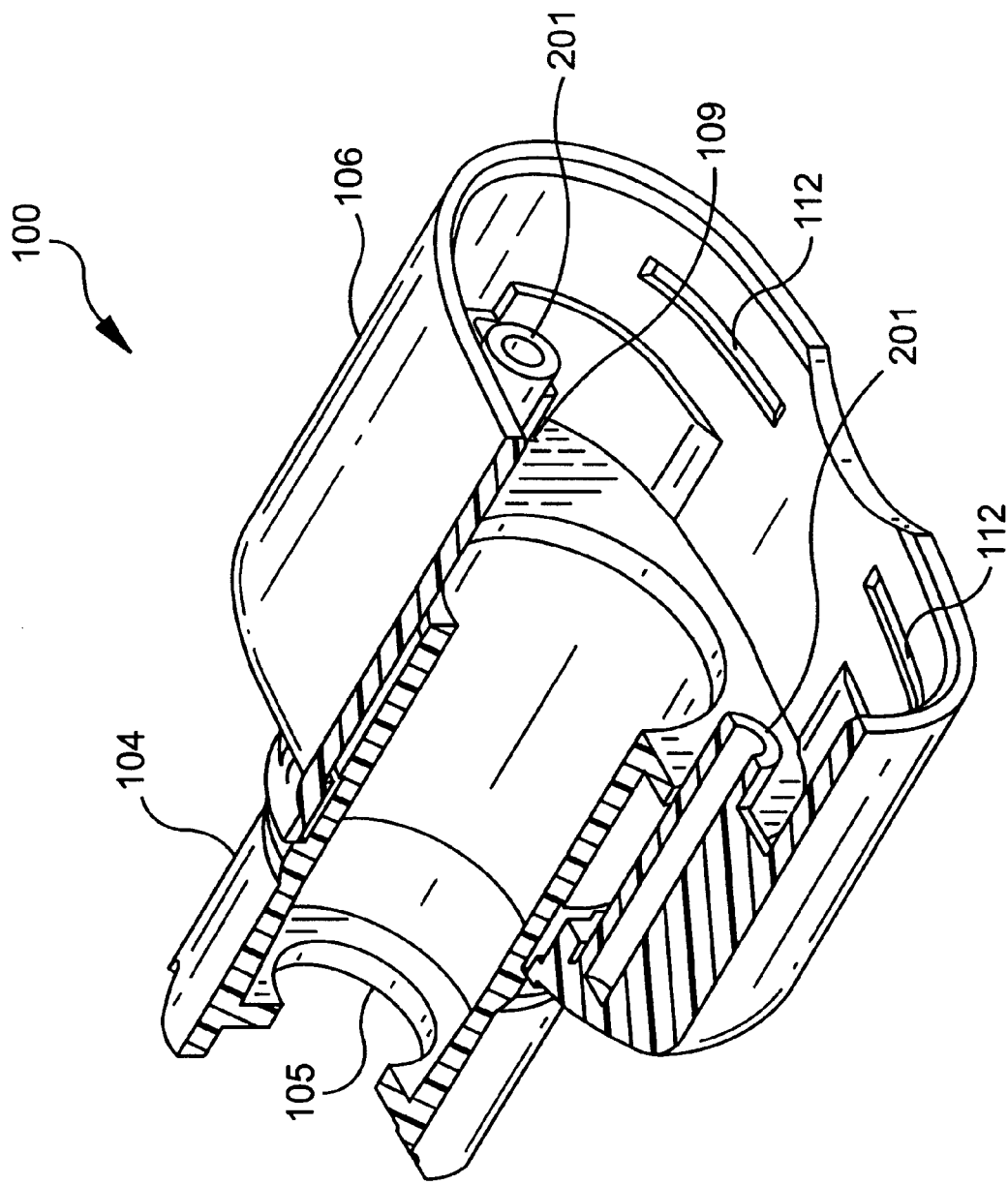
FIG. 4 shows a partial cross-section of the alternate site cap tip.
Figure 5:
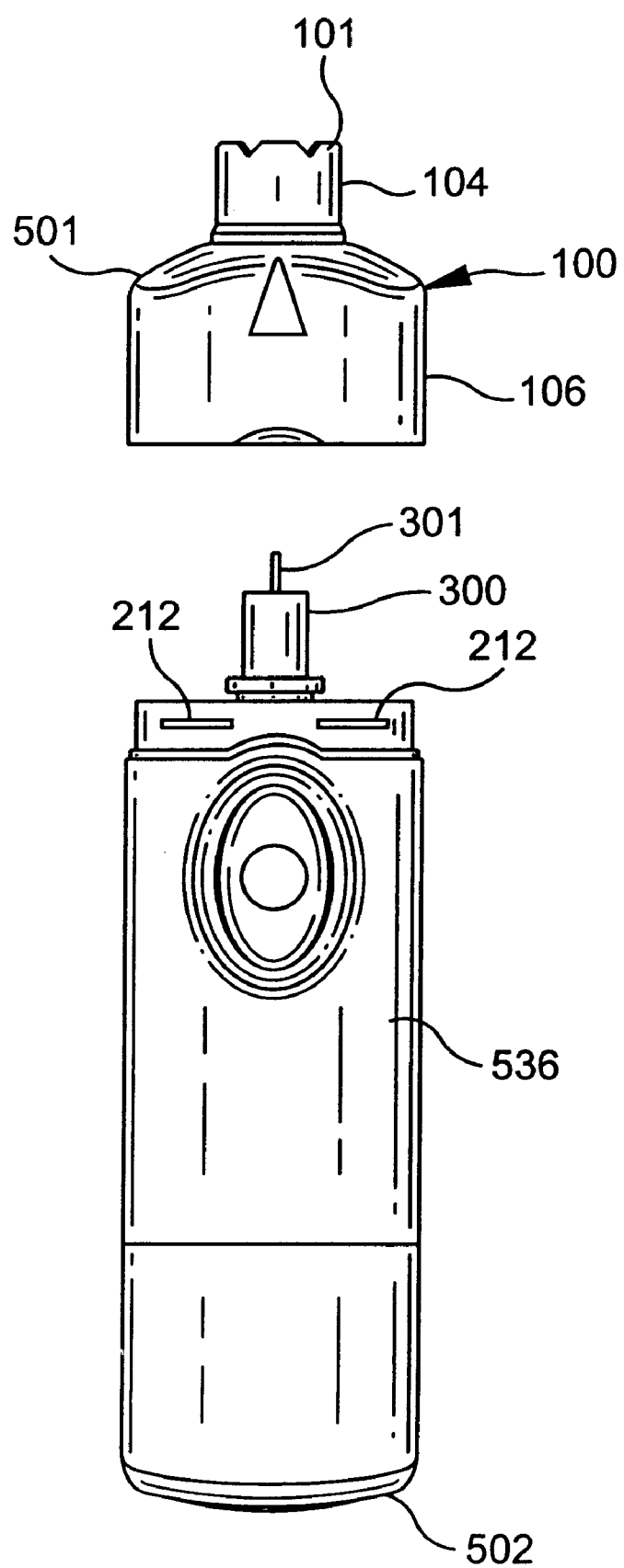
FIG. 5 shows a plan view of the lancer device and alternate cap site tip having a lancet within.

FIG. 4 is a partial cross-section of the alternate site cap tip 100 again showing nose portion 106 with alternate site tip 104 attached therein. FIGS. 3 and 4 show an aperture 105 through which a stylet 301 on the lancet 300, shown in FIG. 5, extends to make the lancet puncture upon activation of lancer 20. FIG. 4 also shows a pair of posts 201 within nose portion 106 that mate with slots 109 in alternate site tip 104 and members 505 that retain alternate site tip 104 within nose portion 106. FIG. 4 also shows detents 112 that mate with detents 212 on body 536 to hold alternate site cap tip 100 on body 536 during use. FIG. 5 shows a plan view of lancer device 20 with alternate site cap tip 100 removed from body 536. FIG. 5 also shows lancet 300 mounted within body 536 and having stylet 301 extending therefrom.

Figure 6:
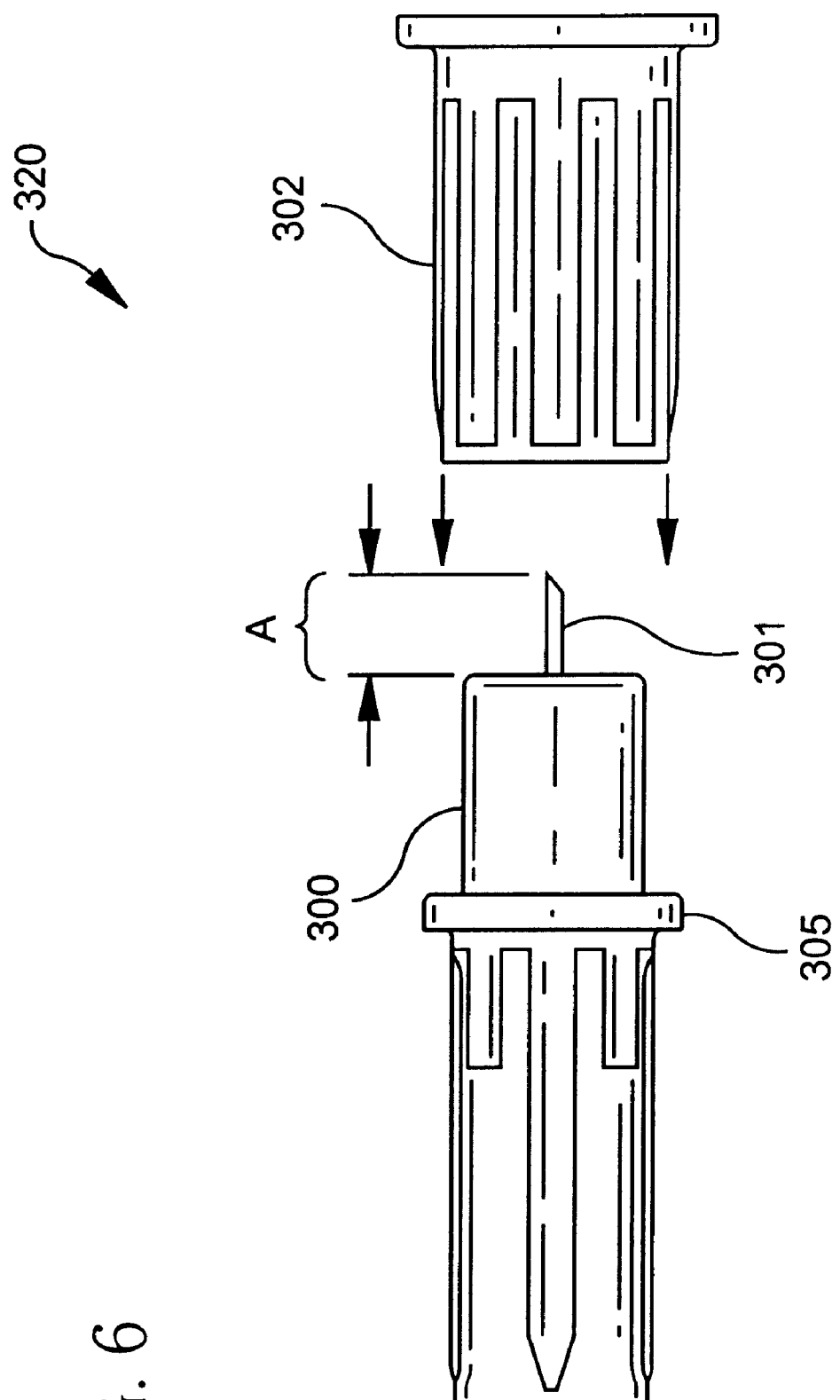
FIG. 6 shows a perspective view of a lancet according to the present invention.
Figure 8:
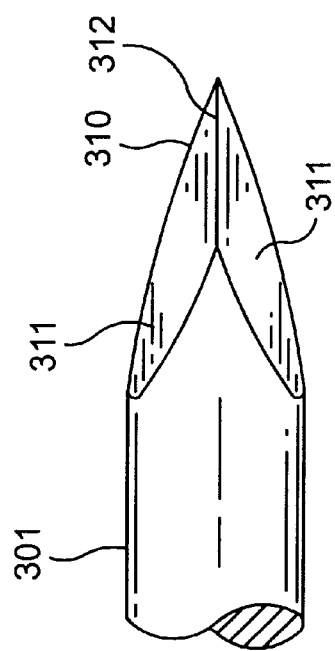
FIGS. 7 and 8 show an enlarged view of the chisel point on the lancet shown in FIG. 6.
Figure 7:
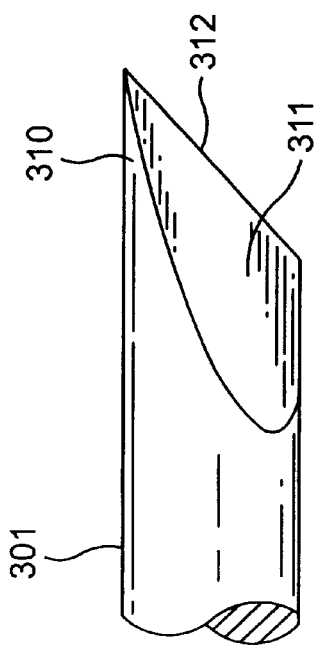

FIG. 6 shows a complete perspective view of lancet 300 including its shield member 302. Shield member 302 is suitably used to cover stylet 301 by interfacing with portion 305 of lancet 300. FIG. 7 shows an enlarged view of a chisel point 310 at the distal end of stylet 301. This is yet another aspect of the present invention used to enhance blood flow when using an alternate site. The new chisel point geometry of chisel point 310 on lancet 300 includes two planar surfaces 311 joined together at a cutting edge 312. The inventors believe that using the chisel point 310 of the present invention at an alternate site improves blood flow and provides a sufficient amount of blood to perform blood analyte testing.

Other variations and modifications of this invention will be obvious to those skilled in this art. This invention is not to be limited except as set forth in the following claims.

What is claimed is:

1. An apparatus attachable to a lancer, said apparatus comprising an alternate site tip having a distal surface with an orifice surrounded by a plurality of crenellations extending in a distal direction, wherein said crenellations exert force on a skin surrounding a lancet puncture site such that when said alternate site tip is rotated blood will freely flow from the lancet puncture site, and wherein each of said plurality of crenellations include a pair of angled ramp surfaces.

2. The apparatus as claimed in claim 1, wherein said pair of angled ramp surfaces are separated by a curved portion.

3. The apparatus as claimed in claim 1, wherein said alternate site tip is transparent.

4. The apparatus as claimed in claim 3, wherein said alternate site tip includes a measuring indicia that is used to determine whether a sufficient amount of blood has been extracted.

5. The apparatus as claimed in claim 1, further comprising a lancet having a chisel point.

6. The apparatus as claimed in claim 1, wherein said alternate site tip is removable from a lancer and replaceable with a conventional site tip.

7. The apparatus as claimed in claim 1, further comprising a nose portion that is attachable to a lancer for holding said alternate site tip.

8. A method for drawing blood from an alternate site on a patient, said alternate site not being a patient's finger, said method comprising the steps of:

providing a lancer with an alternate site tip having a plurality of crenellations extending in a distal direction;

positioning the lancer over an intended lancet puncture site such that the crenellations on the alternate site tip exert force on skin surrounding the lancet puncture site;

activating the lancer to drive the lancet into the lancet puncture site; and rotating the lancer to rotate the crenellations of the alternate site tip and thereby enhance blood flow from the lancet puncture site.

9. The method as claimed in claim 8, further comprising the step of providing each crenellation with a pair of angled ramp surfaces.

10. The method as claimed in claim 9, further comprising the step of providing for each pair of angled ramp surfaces to be separated by a curved portion.

11. The method as claimed in claim 8, further comprising the step of determining whether a sufficient amount of blood has been extracted using a measuring indicia on the alternate site tip.

12. The method as claimed in claim 8, further comprising the step of removing the alternate sit tip from the lancer and mounting a conventional site tip on the lancer.

13. The method as claimed in claim 8, further comprising the step of providing a lancet having a chisel point.

* * * * *